(12) United States Patent
Yamagata et al.

(10) Patent No.: US 9,730,666 B2
(45) Date of Patent: Aug. 15, 2017

(54) MEDICAL IMAGE PROCESSING APPARATUS AND MEDICAL IMAGE PROCESSING METHOD

(71) Applicants: Toshiba Medical Systems Corporation, Otawara-shi (JP); NATIONAL UNIVERSITY CORPORATION KOBE UNIVERSITY, Kobe-shi (JP)

(72) Inventors: Hitoshi Yamagata, Otawara (JP); Yoshiharu Ohno, Kobe (JP)

(73) Assignees: Toshiba Medical Systems Corporation, Otawara-shi (JP); NATIONAL UNIVERSITY CORPORATION KOBE UNIVERSITY, Kobe-shi (JP)

( * ) Notice: Subject to any disclaimer, the term of this patent is extended or adjusted under 35 U.S.C. 154(b) by 32 days.

(21) Appl. No.: 14/875,112

(22) Filed: Oct. 5, 2015

(65) Prior Publication Data
US 2016/0022240 A1 Jan. 28, 2016

Related U.S. Application Data (63) Continuation of application No. PCT/JP2014/058116, filed on Mar. 24, 2014.

(30) Foreign Application Priority Data

Apr. 5, 2013 (JP) .................................. 2013-079896

(51) Int. Cl.
*G06K 9/00* (2006.01)
*A61B 6/00* (2006.01)
(Continued)

(52) U.S. Cl.
CPC ............ *A61B 6/5264* (2013.01); *A61B 6/032* (2013.01); *A61B 6/486* (2013.01); *A61B 6/50* (2013.01);
(Continued)

(58) Field of Classification Search
CPC .... A61B 5/00; A61B 6/00; G06K 9/00; G06T 7/00
(Continued)

(56) References Cited

U.S. PATENT DOCUMENTS 8,821,418 B2 * 9/2014 Meger .................. A61B 5/0002
600/595
2004/0101182 A1 5/2004 Miller et al.
(Continued)

FOREIGN PATENT DOCUMENTS

JP 2004-174263 A 6/2004
JP 2005-20719 A 1/2005
(Continued)

OTHER PUBLICATIONS

Galban, C. et al., "Computed Tomography-Based Biomarker Provides Unique Signature for Diagnosis of COPD Phenotypes and Disease Progression", Nature Medicine, vol. 18, 2012, pp. 1711-1715.
(Continued)

*Primary Examiner* — Abolfazl Tabatabai
(74) *Attorney, Agent, or Firm* — Oblon, McClelland, Maier & Neustadt, L.L.P.

(57) ABSTRACT

According to one embodiment, a medical image processing apparatus includes an image storage memory, a calculation circuitry, a level decision circuitry, and an output interface circuitry. The image storage memory stores data of a plurality of images in different respiratory phases. The calculation circuitry calculates a motion amount of a region
(Continued)

between the plurality of images for each pixel or area. The level decision circuitry decides a level concerning a severity of chronic obstructive pulmonary disease for each pixel or area. The output interface circuitry outputs information concerning the decided level.

25 Claims, 11 Drawing Sheets

(51) Int. Cl.

| | | |
|---|---|---|
| *A61B 6/03* | (2006.01) | |
| *G06T 7/00* | (2017.01) | |
| *G06T 7/20* | (2017.01) | |
| *G06T 11/00* | (2006.01) | |
| *G06T 15/08* | (2011.01) | |
| *A61B 5/05* | (2006.01) | |
| *A61B 5/055* | (2006.01) | |

(52) U.S. Cl.
CPC .......... *A61B 6/5217* (2013.01); *A61B 6/5229* (2013.01); *A61B 6/5235* (2013.01); *G06T 7/0012* (2013.01); *G06T 7/2006* (2013.01); *G06T 11/003* (2013.01); *G06T 15/08* (2013.01); *A61B 5/055* (2013.01); *G06T 2200/04* (2013.01); *G06T 2207/10081* (2013.01); *G06T 2207/30061* (2013.01); *G06T 2210/41* (2013.01); *G06T 2211/40* (2013.01)

(58) Field of Classification Search
USPC ....... 382/128, 129, 130, 131, 132, 133, 134; 378/62, 484, 529, 533; 600/300, 407, 600/410, 411, 425, 427
See application file for complete search history.

(56) References Cited

U.S. PATENT DOCUMENTS

| | | |
|---|---|---|
| 2005/0025365 A1 | 2/2005 | Oosawa |
| 2011/0170658 A1 | 7/2011 | Arakita et al. |
| 2011/0190626 A1 | 8/2011 | Mizuno |
| 2011/0243403 A1 | 10/2011 | Mizuno |
| 2012/0300904 A1 | 11/2012 | Shimada et al. |
| 2013/0156158 A1 | 6/2013 | Noji et al. |
| 2013/0156267 A1 | 6/2013 | Muraoka et al. |

FOREIGN PATENT DOCUMENTS

| | | |
|---|---|---|
| JP | 2009-153677 A | 7/2009 |
| JP | 2011-212312 A | 10/2011 |
| JP | 2011-212313 A | 10/2011 |
| JP | 2012-115582 A | 6/2012 |
| WO | WO 2012/026145 A1 | 3/2012 |
| WO | WO 2012/026146 A1 | 3/2012 |
| WO | WO 2012/176114 A1 | 12/2012 |

OTHER PUBLICATIONS

Watabe, Y., et al., "Quantitative Analysis of Pulmonary Functions by Use of Registration Method from Inspiration and Expiration Thoracic CT Images," *IEICE Technical Report*, Jan. 2010, vol. 109, No. 407, pp. 437-442.
Miyazaki, M., et al., "Analysis of Respiratory Movement Using 4-Dimensional CT Image," *IEICE Technical Report*, Jul. 2011, vol. 111, No. 121, pp. 13-16.
Galban, C., et al., "CT-based Biomarker provides Unique Signature for Diagnosis of COPD Phenotypes and Disease Progression," *Nat Med.* 2012, vol. 18, pp. 1-15.
International Search Report issued Apr. 22, 2014 for PCT/JP2014/058116 filed on Mar. 24, 2014 with English Translation.
Written Opinion issued Apr. 22, 2014 for PCT/JP2014/058116 filed on Mar. 24, 2014.

\* cited by examiner

Chest CT image at time of inspiration
(CT image at time of maximum volume)

FIG. 3

Chest CT image at time of expiration
(CT image at time of minimum volume)

FIG. 4

Segment segmentation

MEDICAL IMAGE PROCESSING APPARATUS AND MEDICAL IMAGE PROCESSING METHOD

CROSS-REFERENCE TO RELATED APPLICATIONS

This application is a Continuation Application of PCT Application No. PCT/JP2014/058116, filed Mar. 24, 2014 and based upon and claims the benefit of priority from prior Japanese Patent Application No. 2013-079896, filed Apr. 5, 2013, the entire contents of which are incorporated herein by reference.

FIELD

Embodiments described herein relate generally to a medical image processing apparatus and a medical image processing method.

BACKGROUND

The embodiments relate to Chronic Obstructive Pulmonary Disease (COPD) diagnosis and, more particularly, to an image diagnostic apparatus using chest CT images. COPD is a disease involving chronic bronchitis and emphysema. In the United States, in particular, COPD is the fourth leading cause of death of persons aged from 65 to 84 years, following the three major diseases (cancer, heart disease, and stoke), and is expected to become the third leading cause of death in place of stoke by the year 2020. Chronic bronchitis indicates persistent or recurrent excess bronchial mucus secretion in the bronchi because of a chronic inflammation of the trachea or bronchi. With regard to a bronchial structure, the fibrous tissue narrows the lumen. In addition, emphysema is a state in which the peripheral alveoli/alveolar duct are destroyed and fused to produce bulla to result in the loss of elasticity. Both the diseases are disorders in which the peripheral small bronchi inflated by the tension of the alveoli are obstructed to result in a deterioration in expiratory ability.

COPD clinical diagnosis is performed by spirometry using the expiratory flow rates measured by a spirometer as a respiratory function examination device. In this case, COPD is diagnosed if the ratio (1 second ratio: FEV1%) of the expiratory volume 1 sec after the administration of a bronchodilator to the forced vital capacity (FVC) is less than 70%. In addition, the severity of COPD is diagnosed based on the ratio (%1 second ratio: % FEV1) of the FEV1 to the standard FEV1. Severities are expressed by Global Initiative for Chronic Obstructive Lung Disease (GOLD) values (GOLD 0 (risk group) to GOLD 4 (most severe)) defined by an international project called GOLD. COPD diagnosis by this spirometry is limited to the diagnosis of an overall lung field function. For this reason, in order to make a treatment strategy, treatment effect determination, and follow-up, there are demands for local or localized COPD diagnosis for each pixel of a medical image or for each lung area such as a lung lobe or pulmonary segment.

Under the circumstances, there has already been realized a technique of expressing the degree of local COPD by presenting a Low Attenuation Area (LAA) representing a change in the above bronchial structure and the presence of bulla caused by COPD using a chest CT image at the time of expiration. However, since this technique is designed to perform determination based on a given threshold (e.g., −950 HU) at a given CT value, the technique cannot be said to be an accurate diagnosis technique because CT values are not always common to all CT apparatuses. In order to solve this problem, as observation methods, there have been proposed a method of presenting a movement amount for each voxel obtained from the registration information obtained by performing registration between an expiration image and an inspiration image of chest CT images and a method of performing determination based on CT values obtained at the time of expiration and at the time of inspiration for each voxel upon registration (non-patent literature 1). The latter method is designed to set −950 HU for inspiration images and −856 HU for expiration images in a two-dimensional coordinate space having, as two axes, CT values (x-axis) at the time of expiration and CT values (y-axis) at the time of inspiration, and to perform determination on a pixel basis by setting normal, COPD (substantially equivalent to emphysema), and functional Small Airways Disease (fSAD) as an intermediate disease state between them with respect to the four formed quadrants.

It is however difficult to accurately determine the degree of COPD from only the motions of voxels or CT values using expiration and inspiration images of the chest CT images described above.

DETAILED DESCRIPTION

In general, according to one embodiment, a medical image processing apparatus includes an image storage memory, a calculation circuitry, a level decision circuitry, and an output interface circuitry. The image storage memory stores data of a plurality of images in different respiratory phases which represent a morphology of an object chest portion. The calculation circuitry calculates a motion amount of a region between the plurality of images for each pixel or area. The level decision circuitry decides a level concerning a severity of chronic obstructive pulmonary disease for each pixel or area based on a combination of at least two of the motion amount, a feature value obtained from pixel values of the image, and a change rate of a size of the area. The output interface circuitry outputs information concerning the decided level.

A medical image processing apparatus according to this embodiment will be described below with reference to the accompanying drawings. The following description will exemplify volume data representing the three-dimensional morphology (three-dimensional structure) of the interior of an object chest area. An X-ray computed tomography apparatus or magnetic resonance imaging apparatus generates the volume data. Note that the medical image processing apparatus according to the embodiment may use, as a processing target, a tomographic image representing the two-dimensional morphology (two-dimensional structure) of the interior of an object chest area. Assume that the simple term "image" will indicate "volume data or two-dimensional image (tomographic image) data" hereinafter. Assume also that the simple term "pixel" will indicate "a voxel of volume data or a pixel of a two-dimensional image (tomographic image)" hereinafter.

Figure 1:
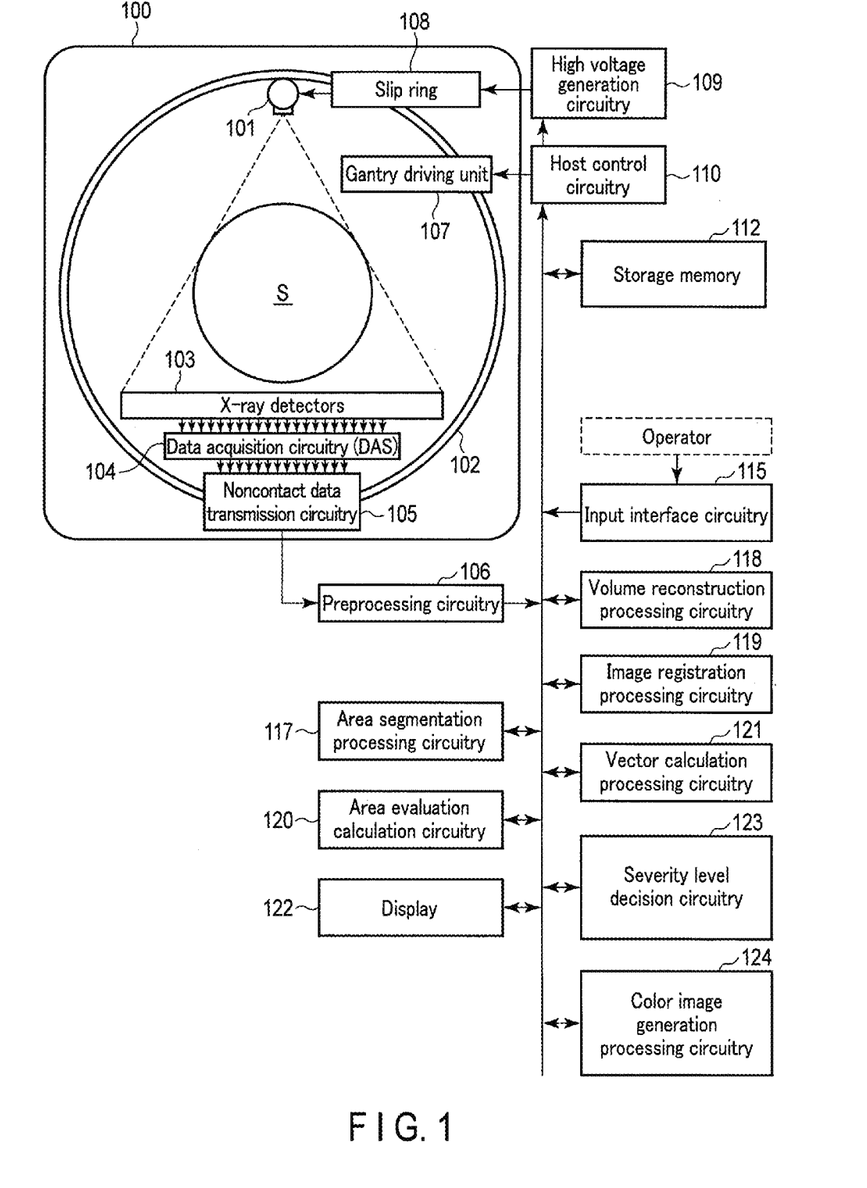
FIG. 1 is a block diagram showing a medical image processing apparatus according to this embodiment, together with an X-ray computed tomography apparatus.

As shown in FIG. 1, the medical image processing apparatus according to this embodiment is used by itself or incorporated in an X-ray computed tomography apparatus. The embodiment will be described as a rotate/rotate-type apparatus in which an X-ray tube 101 and an X-ray detector 103 rotate together around an object. However, this apparatus may include various types of apparatuses, e.g., a stationary/rotate-type apparatus in which many X-ray detectors 103 are arranged on a ring, and only the X-ray tube 101 rotates around an object, and a stationary/stationary-type apparatus in which a plurality of X-ray tubes 101 are arranged on a ring and a plurality of X-ray detectors 103 are also arranged on the ring. A rotate/rotate-type apparatus will be described as a single tube apparatus in which a pair of the X-ray tube 101 and the X-ray detector 103 are mounted on a rotating frame. However, this apparatus may be a so-called multi-tube type apparatus in which a plurality of pairs of X-ray tubes 101 and X-ray detectors 103 are mounted on a rotating frame. The X-ray detectors 103 include an indirect conversion type that converts X-rays transmitted through an object into light through a phosphor such as a scintillator and converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. The embodiment may use either type.

A gantry unit (also called a gantry) 100 includes a rotating ring 102. A gantry driving unit 107 rotates the rotating ring 102 under the control of a host control circuitry 110. The X-ray tube 101 and the X-ray detector 103 are mounted on the rotating ring 102. The X-ray detector 103 faces the X-ray tube 101 through an imaging area S into which an object is inserted by a top slide. A high voltage generation circuitry 109 is processing circuitry that generates a tube voltage to be applied between the two electrodes of the X-ray tube 101, and generates a tube current to be supplied to a cathode filament. When the high voltage generation circuitry 109 applies a tube voltage and supplies a tube current to the X-ray tube 101 via a slip ring 108, the X-ray tube 101 generates X-rays. The high voltage generation circuitry 109 reads a program corresponding to a high voltage generation function from a storage memory 112, and executes the program to realize the high voltage generation function. A collimator (also called an X-ray stop device) (not shown) shapes the X-rays generated by the X-ray tube 101 into, for example, a cone beam shape. As the X-ray detector 103, a multi-array detector (also called a multi-slice detector) is used to receive a cone-shaped X-ray beam. Data acquisition circuitry 104 generally called a DAS (Data Acquisition System) is connected to the X-ray detectors 103. The data acquisition circuitry 104 is provided with, for each channel, an I-V converter which converts the current signal obtained via each channel of the X-ray detector 103 into a voltage, an integrator which periodically integrates these voltage signals in synchronism with an X-ray irradiation period, an amplifier which amplifies an output signal from the integrator, and an analog/digital converter which converts an output signal from the amplifier into a digital signal.

A preprocessing circuitry 106 is connected to the data acquisition circuitry 104 via a noncontact data transmission circuitry 105. The preprocessing circuitry 106 is processing circuitry that, in response to the data received from the data acquisition circuitry 104, performs preprocessing such as sensitivity nonuniformity correction between channels and correcting an extreme decrease in signal intensity or signal dropout caused by an X-ray strong absorber, mainly a metal portion. The preprocessing circuitry 106 reads a program corresponding to a preprocessing function from the storage memory 112, and executes the program to realize the preprocessing function.

The storage memory 112 stores the projection data having undergone preprocessing by the preprocessing circuitry 106, reconstructed volume data and tomographic image data, and the like. A reconstruction processing circuitry 118 is processing circuitry that reconstructs volume data and tomographic image data based on stored projection data. The reconstruction processing circuitry 118 reads a program corresponding to a reconstruction function from a storage memory 112, and executes the program to realize the reconstruction function. A display 122 mainly displays images or color images (to be described later).

The medical image processing apparatus according to this embodiment processes a plurality of images in different respiratory phases. This apparatus typically uses the first volume data acquired in an expiratory phase in which each lung field exhibits the smallest volume and the second volume data acquired in an inspiratory phase in which each lung field exhibits the maximum volume.

An image registration processing circuitry 119 is processing circuitry that matches (registers) anatomically identical targets of the first volume data and the second volume data at the same position. The image registration processing circuitry 119 reads a program corresponding to a registration processing function from a storage memory 112, and executes the program to realize the registration processing function. In practice, the image registration processing circuitry 119 performs registration between the first volume data at the time of expiration and the second volume data at the time of inspiration. In addition, the image registration processing circuitry 119 is also used to perform the registration processing of anatomically registering the expiration volume data or inspiration volume data with standard expiration or inspiration chest volume data. This registration processing is performed by registration at the voxel level using a so-called non-rigid registration technique. Non-rigid registration is the operation of associating anatomically identical pixels (voxels) in consideration of the displacement and deformation of each lung field caused by the respiration of the object. That is, non-rigid registration processing can be regarded as the processing of correcting the distortion between targets on volume data as well as registration between the targets. In practice, this processing uses, for example, a technique of deforming an expiration image by performing lung area extraction, bronchial area extraction, or pulmonary artery area extraction and generating a warp field indicating the displacement direction and distance of each area in an expiration image space from the differences between expiration and inspiration images of the extracted areas. Basically, the non-rigid registration technique disclosed in Jpn. Pat. Appln. KOKAI Publication No. 2012-179359 is applied to the processing.

An area segmentation processing circuitry 117 is processing circuitry that extracts a lung field area from each of the first and second volume data by dilation/erosion processing using, for example, a CT value corresponding to an aerated lung area as a threshold, and segments the extracted lung field area into a plurality of areas. For example, a lung field area is segmented into a left lung area and a right lung area. The left and right lung areas are further segmented such that the right lung is segmented into three lung lobe areas including an upper lobe area, a middle lobe area, and a lower lobe area, and the left lung is segmented into two lung lobe areas including an upper lobe area and a lower lobe area by using a CT value corresponding to a lung lobe mesenteriolum. Each lung lobe area is further segmented into segmented areas as smaller units based on the branching of lobe bronchi identified by processing such as a pattern matching technique using the bronchi and the branching structure of pulmonary arteries accompanying the bronchi. Typically, the right lung is segmented into 10 segment areas, and the left lung is segmented into nine segment areas. The area segmentation processing circuitry 117 reads a program corresponding to a segmentation processing function from a storage memory 112, and executes the program to realize the segmentation processing function. Note that an operator or the like arbitrarily selects, via an input interface circuitry 115, a left/right lung area, a lung lobe area, a segmented area, a voxel unit, or a block area as an aggregate (e.g., a cube) constituted by a predetermined number of adjacent voxels as a target subjected to vector processing (to be described later). As the input interface circuitry 115, input devices such as a mouse, keyboard, trackball, touch panel, and button are properly usable.

A vector calculation processing circuitry 121 is processing circuitry that calculates the displacement direction and displacement distance of a target, i.e., a motion vector, for each voxel, between the first and second volume data in different respiration periods. The vector calculation processing circuitry 121 reads a program corresponding to a vector calculation processing function from a storage memory 112, and executes the program to realize the vector calculation processing function. If the target is a segmented area such as the above block area or lobe area, the vector calculation processing circuitry 121 generates a single motion vector from a plurality of motion vectors concerning a plurality of voxels in each area. For example, the vector calculation processing circuitry 121 obtains an average vector of a plurality of motion vectors of each area or selects a representative motion vector, from a plurality of motion vectors, whose displacement distance indicates an intermediate value or median value.

An area evaluation value calculation circuitry 120 is processing circuitry that calculates an evaluation value indicating a feature of a CT value distribution in each area for each segmented area such as the above block area or lobe area. Evaluation values (feature values) typically include the ratio (% LAV: percentage of Low Attenuation Volume) of the number of voxels exhibiting less than −950 HU corresponding to air or a gas to the total number of voxels in each area and the average value, variance value, skewness, and kurtosis of CT values obtained from a CT value distribution (CT value histogram) in each area. Another example of a feature value to be used includes a pixel value, a pixel value difference, the ratio of the number of pixels having pixel values less than a threshold to the number of pixels in an area, the variance of a pixel value distribution in an area, or the average value of pixel values in an area. An operator or the like arbitrarily selects one of evaluation values as a processing target. The area evaluation value calculation circuitry 120 reads a program corresponding to an area evaluation value calculation function from a storage memory 112, and executes the program to realize the area evaluation value calculation function.

Figure 16:
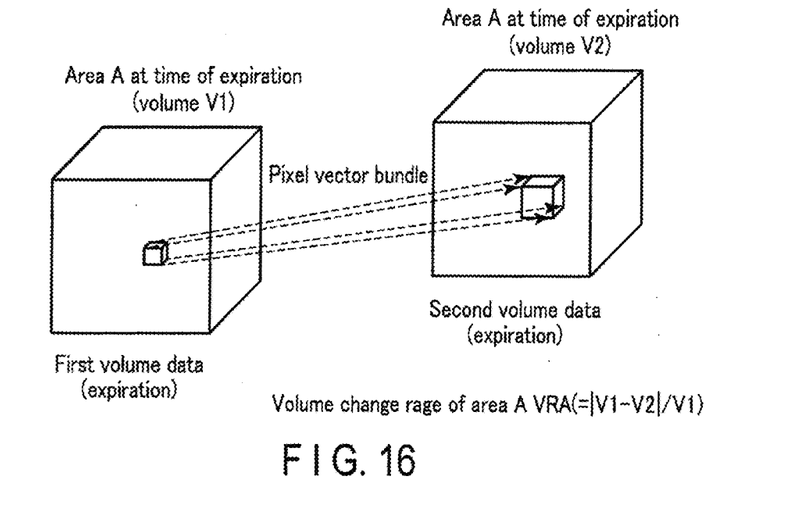
FIG. 16 is a view showing a volume change rate as one of the parameters used to decide a severity level in this embodiment.

The area evaluation value calculation circuitry 120 further calculates the change rate of the size of an area between the first and second volume data, that is, a volume change rate in the case of three dimensions or an area volume change rate in the case of two dimensions. As shown in FIG. 16, a volume change rate VRA of an area A is given by, for example $$|V1-V2|/V1$$

Figure 17:
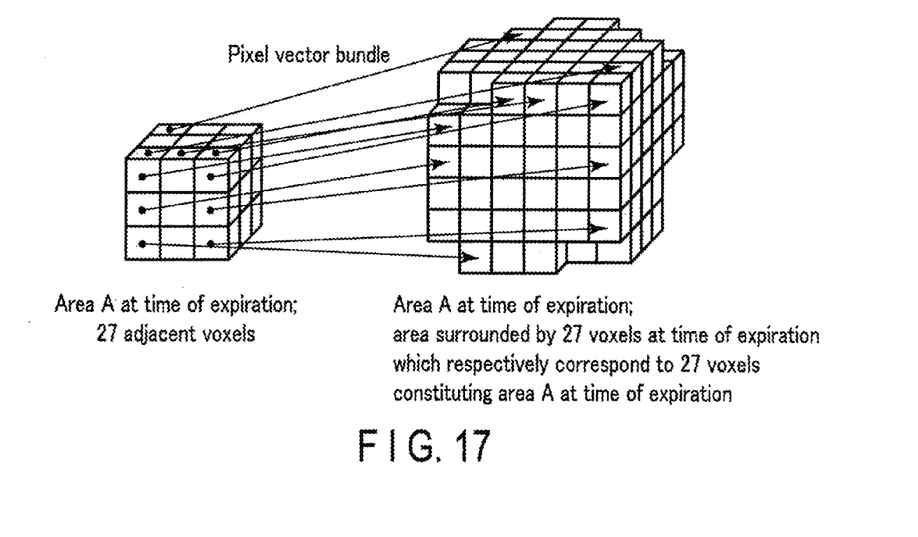
FIG. 17 is a view showing the details of the volume change rate in FIG. 16.

As shown in FIG. 17, V1 represents the volume (or area) of the area A defined by a plurality of adjacent pixels (vectors) on the first volume data. In the case of three dimensions, the area A is set in the range of, for example, 27 adjacent pixels. Note that in the case of two dimensions, the area A is set in the range of nine adjacent pixels. A motion vector has been obtained for each of these 27 pixels. The 27 pixels on the first volume data respectively correspond to 27 pixels on the second volume data via motion vectors. The area A at the time of expiration expands at the time of inspiration. The 27 pixels on the second volume data are discrete. V2 represents the volume (or area) of the area A surrounded by the 27 pixels on the second volume data.

A severity level decision circuitry 123 is processing circuitry that decides a level concerning the severity of chronic obstructive pulmonary disease for each pixel or area based on a combination of at least two of any kind of feature value, the motion vector of each voxel (pixel) or area, and the change rate of the size of an area. The severity level decision circuitry 123 reads a program corresponding to a severity level decision function from a storage memory 112, and executes the program to realize the severity level decision function. This operation will be described in detail later.

A color image generation processing circuitry 124 is processing circuitry that generates a three-dimensional color image on which the three-dimensional distribution of severity levels, each decided by the severity level decision circuitry 123 for each voxel, each 4×4×4 block area, or each segmented area, coincides with anatomical positions on the first or second volume data concerning colors assigned in advance in accordance with the severity levels. The color image generation processing circuitry 124 further converts the above three-dimensional color image into two-dimensional color image, which can be displayed on the display 122, by MRP (Multi Planar Reconstruction), volume rendering processing, or the like. The color image generation processing circuitry 124 reads a program corresponding to a color image generation processing function from a storage memory 112, and executes the program to realize the color image generation processing function.

Figure 2:
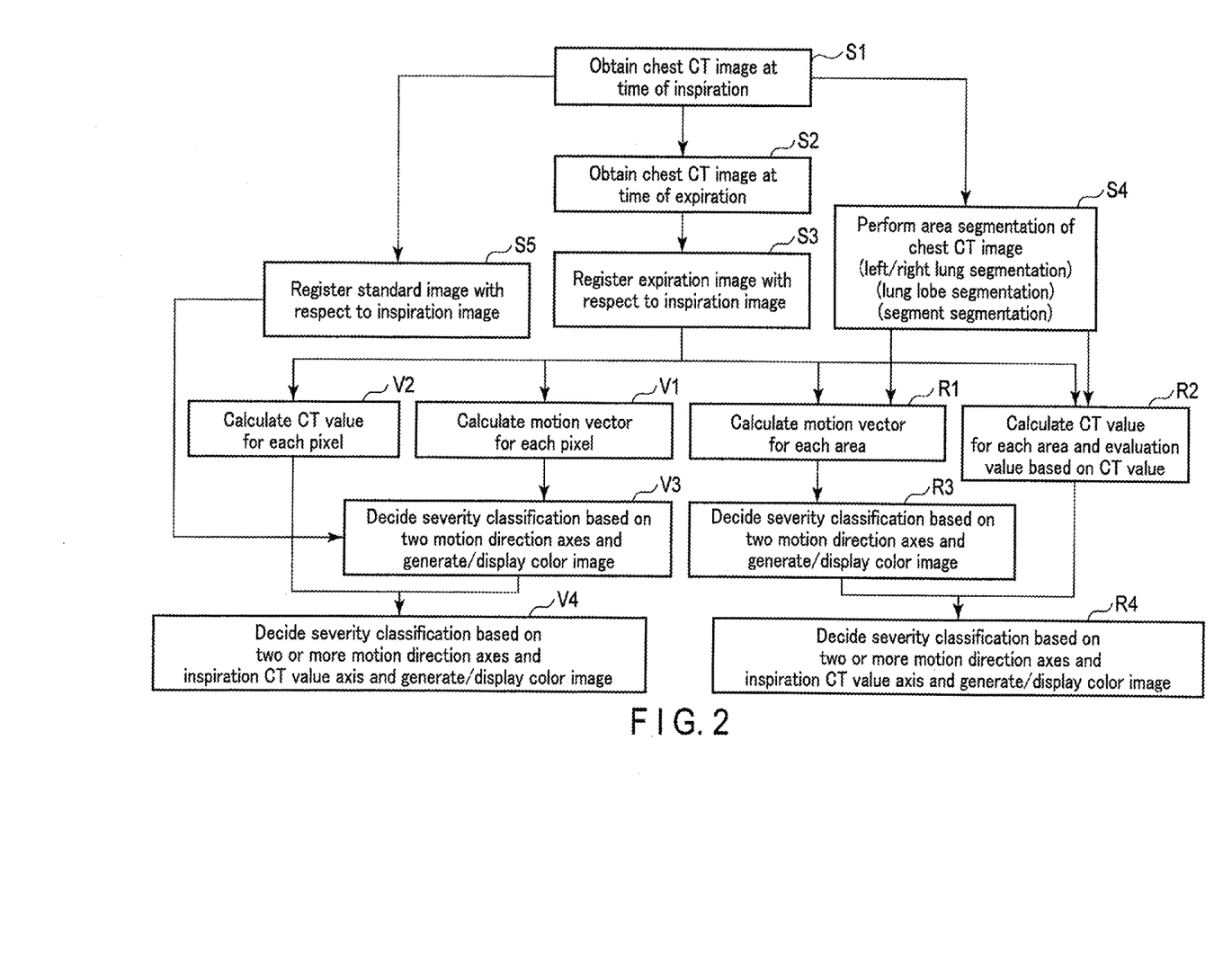
FIG. 2 is a flowchart showing a procedure for medical image processing according to this embodiment.
Figure 3:
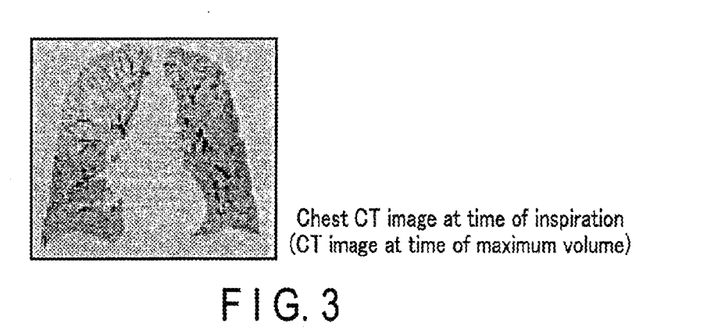
FIG. 3 is a view showing an image example concerning step S1 in FIG. 2.
Figure 4:
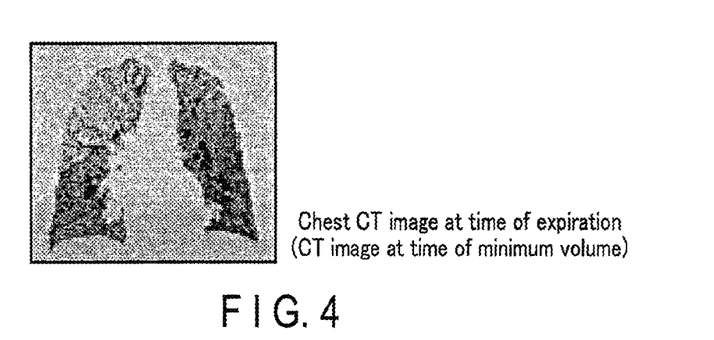
FIG. 4 is a view showing an image example concerning step S2 in FIG. 2.

FIG. 2 shows a medical image processing procedure according to this embodiment. First of all, as shown in FIG. 3, a three-dimensional chest CT image (also called the second volume data) is reconstructed (obtained) based on the projection data acquired at the time of inspiration (at inspiration breath-hold) (step S1). When obtaining an image of the lung fields of an adult, it is necessary to perform imaging in the range of 40 cm in the body axis direction. In general, both MSCT scanning and helical scanning are performed by using the two-dimensional detector 103 compatible with multi-slice imaging. Likewise, as shown in FIG. 4, a three-dimensional chest CT image (the first volume data) is reconstructed based on the projection data acquired at the time of expiration (at expiration breath-hold) (step S2).

The chest CT image (the second volume data) at the time of inspiration and the chest CT image (the first volume data) at the time of expiration are sent to the image registration processing circuitry 119 via the storage memory 112, thereby registering the chest CT image (the second volume data) at the time of expiration with respect to the chest CT image (the first volume data) at the time of inspiration (step S3). Since there is lung field deformation accompanying respiration between the two images, this registration is performed at the voxel level by using a non-rigid registration technique. This registration technique uses, for example, a technique of deforming an expiration image by performing lung area extraction, bronchial area extraction, or pulmonary artery area extraction and generating the warp field of an expiration image space from the differences between expiration and inspiration images of the extracted areas.

Figure 5:
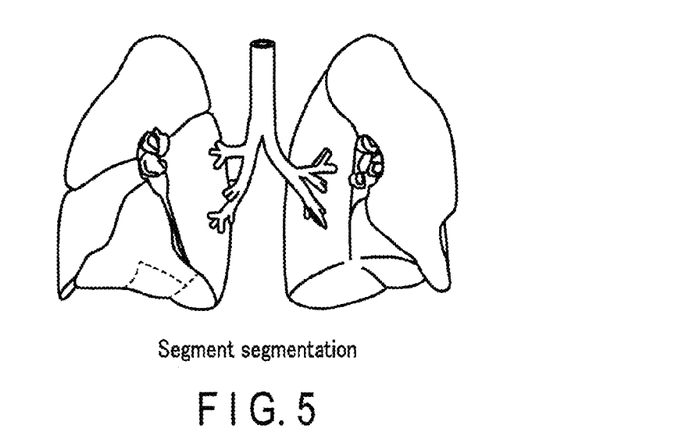
FIG. 5 is a view showing a segment example in step S4 in FIG. 2.

In addition, the chest CT image (the second volume data) at the time of inspiration is sent to the area segmentation processing circuitry 117 via the storage memory 112. The area segmentation processing circuitry 117 extracts a lung field area, and segments the lung field area into a left lung area and a right lung area. As exemplarily shown in FIG. 5, the left and right lung areas are further segmented such that the right lung is segmented into three lung lobe areas including an upper lobe area, a middle lobe area, and a lower lobe area, and the left lung is segmented into two lung lobe areas including an upper lobe area and a lower lobe area. Each lung lobe area is further segmented into segment areas as smaller units based on the branching points of lobe bronchi.

The chest CT image (the second volume data) at the time of inspiration and the chest CT image (the first volume data) at the time of expiration are sent to the image registration processing circuitry 119 via the storage memory 112. The image registration processing circuitry 119 registers the chest CT image (the second volume data) at the time of inspiration with respect to the chest CT image (the first volume data) at the time of expiration (step S3). Since there is lung field deformation accompanying respiration between the two images, this registration is performed at the voxel level by using a non-rigid registration technique. This registration technique uses, for example, a technique of deforming an expiration image by performing lung area extraction, bronchial area extraction, or pulmonary artery area extraction and generating the warp field of an expiration image space from the differences between expiration and inspiration images of the extracted areas.

When performing analysis concerning the motion amounts of voxels (the distances of motion vectors) used in steps V3 and V4 (to be described later), it is necessary to use a table (to be referred to as a severity table hereinafter) indicating a proper severity at each position in a lung structure. For this reason, registration is performed for each voxel or each block area constituted by, for example, 4×4×4 voxels between a standard chest CT image concerning shape/structure and having corresponding proper values and the chest CT image at the time of inspiration. A registration technique similar to the processing in step S3 is used.

The contents of processing will be described below separately with respect to steps V1 to V4 in which a color image is generated on a voxel basis and steps R1 to R4 in which a color image is generated on an area basis. The following is the outline of each process. That is, in the generation of a color image on a voxel basis, pixels are mapped on a preset severity table corresponding to the voxels of the standard image obtained in step S5 based on a combination of at least two of the motion vector amount (displacement distance) of each voxel, one feature value obtained by CT value analysis, and a volume change rate, and colors corresponding to severities are assigned to the respective pixels, thereby performing color display. In the generation of a color image on an area basis, one value obtained by analysis on an evaluation value such as the percentage of low attenuation volume using a motion vector as an area and the CT value which can be calculated in each area is mapped on a severity table corresponding to each segmented area obtained in step S4 or each block area of the standard image obtained in step S5, and colors corresponding to severities are assigned to the respective areas, thereby performing color display.

The above preset severity table is generated by performing the same processing (steps S1 to S5, V1 and V2, and R1 and R2) for the clinical data obtained in advance and having undergone many GOLD evaluations and performing principal component analysis with GOLD evaluations corresponding to combinations of parameters such as motion and CT values.

First of all, in step V1 aiming at processing on a voxel basis, the vector calculation processing circuitry 121 calculates a motion vector at a voxel (pixel) level from two registered chest CT images, and calculates the motion amounts and vector absolute values in the X, Y, and Z directions as the three direction components of the motion vector.

In step V2, the severity level decision circuitry 123 calculates CT values of the inspiration chest CT image and the expiration chest CT image from the two registered chest CT images on a voxel (pixel) basis, and the difference between the CT values. The severity level decision circuitry 123 also calculates the volume change rate of each area between the first and second volume data.

Figure 6:
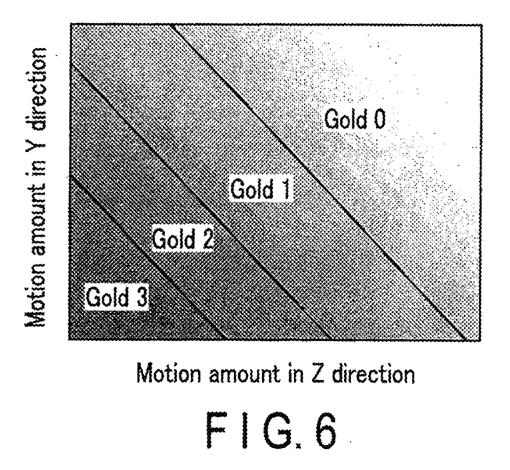
FIG. 6 is a view showing a modification of level specifying processing in steps V3 and R3 in FIG. 2.

In step V3, the severity level decision circuitry 123 decides a severity level on a voxel basis, and a corresponding color image is generated and displayed. In step V3, based on a displacement distance in the displacement direction indicated by the motion vector of each voxel and two direction components of three direction components (distances) concerning the three orthogonal axes, i.e., the X-, Y-, and Z-axes, concerning the motion vector, a severity level is decided (classified) for each voxel from the viewpoint of the movement of each portion accompanying respiration by mapping an analysis value of each voxel on the above severity table obtained in advance. For example, as shown in FIG. 6, four severity levels (stages), i.e., Gold 0 to Gold 3, are decided on a voxel basis from motion amounts (movement distances) in the Y direction and motion amounts in the Z direction. For example, severity increases from Gold 0 to Gold 3.

Figure 7:
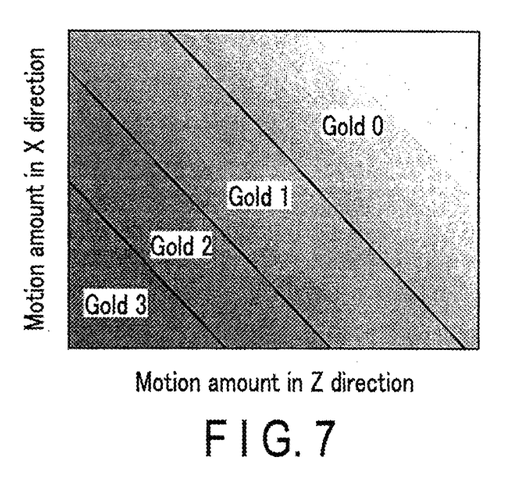
FIG. 7 is a view showing the modification of level specifying processing in steps V3 and R3 in FIG. 2.
Figure 8:
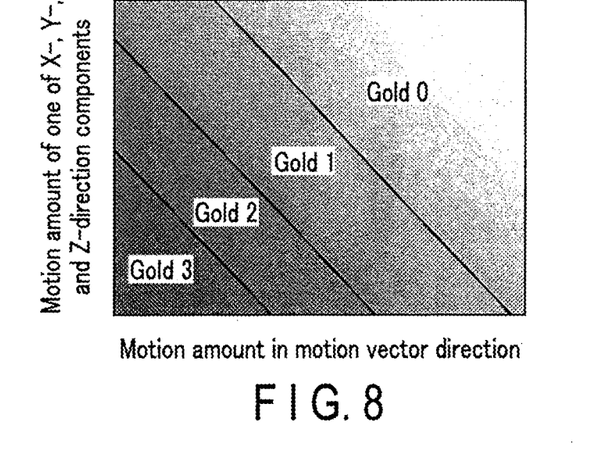
FIG. 8 is a view showing the modification of level specifying processing in steps V3 and R3 in FIG. 2.

As shown in FIG. 7, a severity level may be decided from a motion amount in the X direction and a motion amount in the Z direction. Alternatively, as shown in FIG. 8, a severity level may be decided from a motion amount in one of the X, Y, and Z directions and a motion amount in the motion vector direction.

Figure 14:
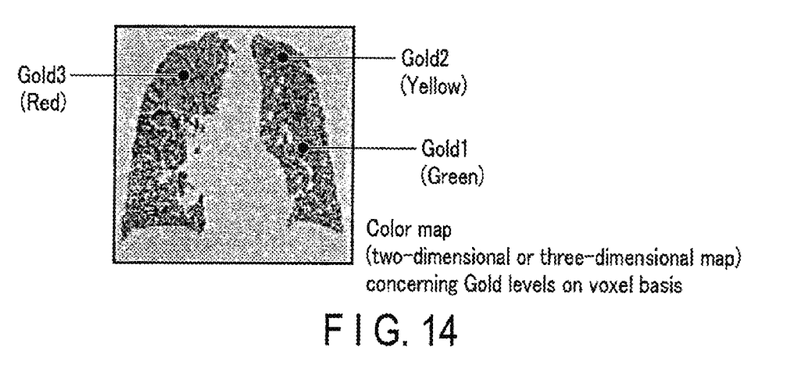
FIG. 14 is a view showing an image example concerning step V4 in FIG. 2.

A color image is generated by assigning colors corresponding to severity levels decided for the respective voxels on the first inspiration chest CT image, and is displayed, as shown in FIG. 14. In this severity/color assignment, different colors are assigned to four severity levels such that, for example, red is assigned to severity level Gold 3, and green is assigned to Gold 0. Alternatively, continuous gradations from red to green may be set from Gold 3 to Gold 0. Although four levels from Gold 0 to Gold 3 are set in this example, area segmentation may be performed with five steps from Gold 0 to Gold 4.

According to the above description, a severity level concerning the severity of obstructive pulmonary disease is decided based on the displacement distance indicated by a vector and two parameters among three direction components concerning the three orthogonal axes, i.e., the X-, Y-, and Z-axes, concerning the motion vector. However, a severity level may be decided based on three parameters among a motion vector amount and the like.

Figure 9:
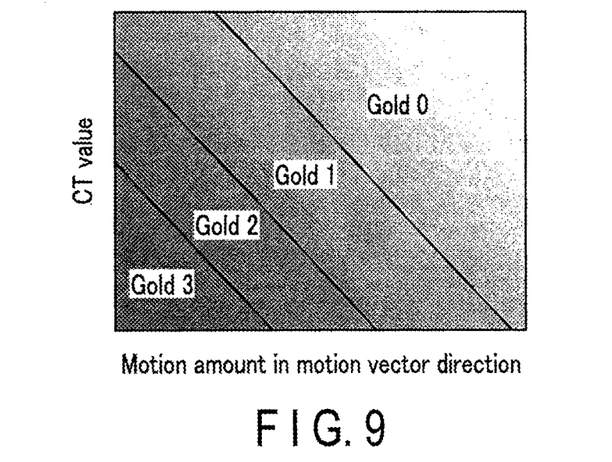
FIG. 9 is a view showing the modification of level specifying processing in steps V3 and R3 in FIG. 2.
Figure 10:
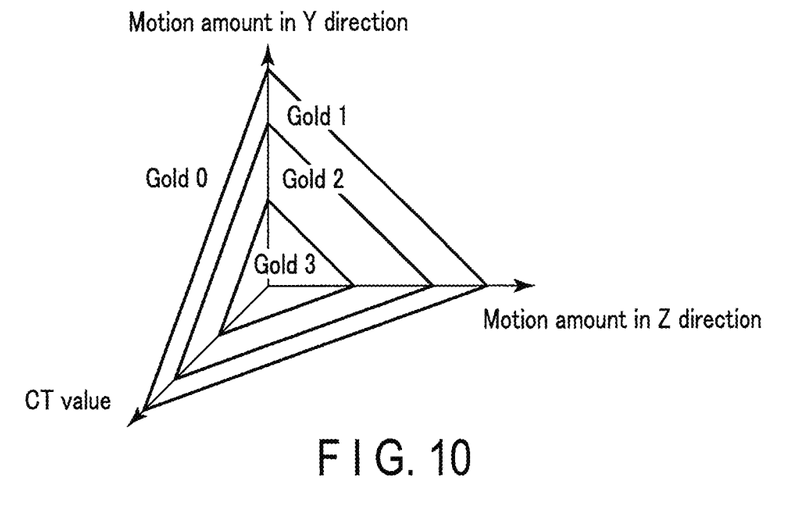
FIG. 10 is a view showing an example of level specifying processing in steps V3 and R3 in FIG. 2.
Figure 11:
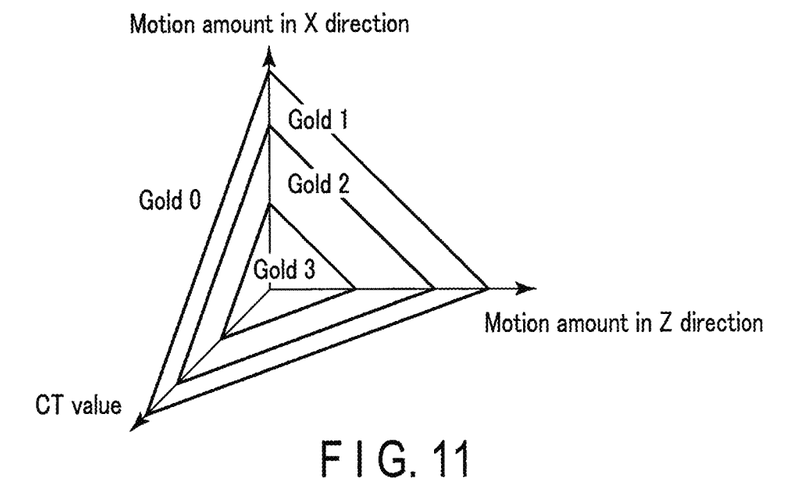
FIG. 11 is a view showing another example of level specifying processing in steps V3 and R3 in FIG. 2.
Figure 12:
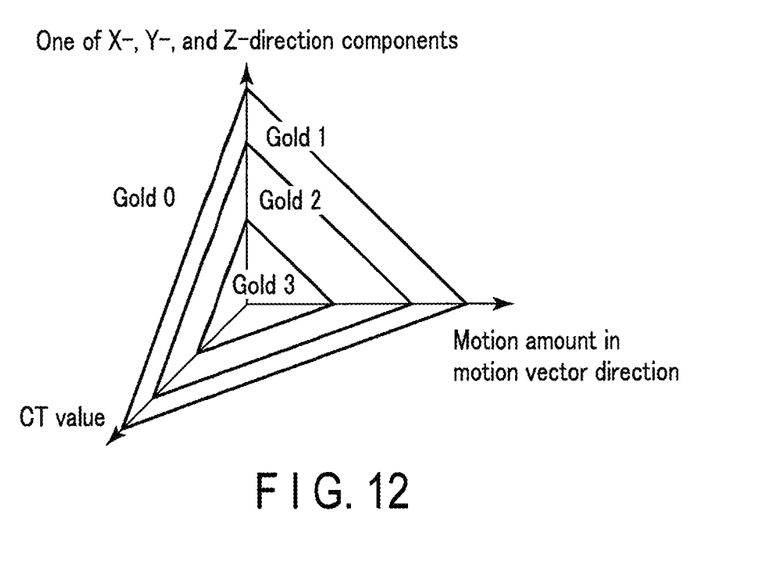
FIG. 12 is a view showing still another example of level specifying processing in steps V3 and R3 in FIG. 2.
Figure 13:
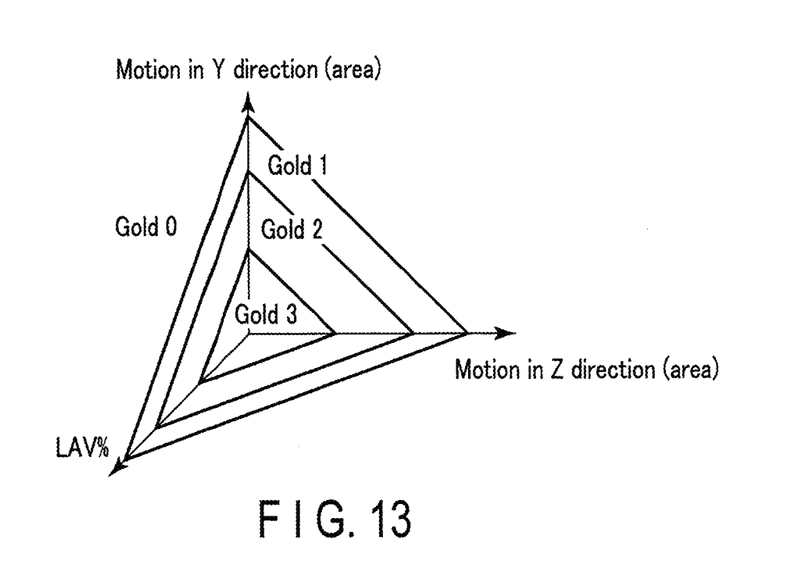
FIG. 13 is a view showing still another example of level specifying processing in steps V3 and R3 in FIG. 2.

In step V4, with regard to the motion of each voxel as in the above case, a severity level is decided by using a motion vector amount in the motion vector direction, one or more motion direction components selected from three direction components concerning the three orthogonal axes, i.e., the X-, Y-, and Z-axes, concerning the motion vector, and the feature value obtained from a CT value. For example, as shown in FIG. 9, a severity level may be decided from a motion amount in one of the X, Y, and Z directions or a motion amount in the motion vector direction and a CT value of one of the two chest CT images or a difference value between them. Referring to FIG. 10, a level is decided in accordance with the four areas determined from three parameters including a motion amount in the z direction, a motion amount in the y direction, and a CT value or the CT value difference between the two images as the third axis. Referring to FIG. 11, a CT value may be set as the third axis with respect to a motion amount in the z direction and a motion amount in the x direction. Referring to FIG. 12, a CT value may be set as the third axis with respect to the motion amount of a voxel in the vector direction (i.e., the absolute value of the motion vector) and the maximum amount of one of direction components in the x, y, and z directions.

A color image is generated by assigning a color corresponding to the severity level decided for each voxel from two or three parameters in this manner on the first inspiration chest CT image, and is displayed as shown in FIG. 14. In this color setting, colors may be independently set for four Gold areas, for example, from red for Gold 3 to green for Gold 0, or colors may be continuously changed from red to green from the three-axis intersection of Gold 3 to the front side of Gold 0.

Four parameters may be set by adding a CT value at the time of expiration or the like to the above three parameters. Furthermore, other parameters may be added to set Gold values by using a technique such as principal component analysis in a multidimensional space equal to or more than five dimensions. Colors corresponding to the Gold values are set as color values for the corresponding voxels.

The processing of generating a color image by deciding levels on an area basis will be described next. Parameters such as a structure volume (or its change) concerning each segmented area obtained by segmentation in step S4 or each block area and an LAV % value (or its change) representing the ratio of a low-dose area are added to the choices for deciding severity levels.

In step R1, a motion vector is calculated as each area concerning segmented areas of the left and right lungs, lung lobes, or segments obtained in step S4 or block areas. In this calculation, the average value, intermediate value, or the like of the motion vectors of a plurality of vectors concerning a plurality of voxels in each of the above areas is grasped as a motion vector concerning the corresponding area. In step R2, an LAV % value at the time inspiration (for example, a threshold of −950 HU) and LAV % at the time expiration (for example, a threshold of −856 HU) which represent the ratio of a low-dose area in each area are obtained from a CT value of each area concerning the left and right lungs, lung lobes, or segments obtained in step S4 or each block area. Alternatively, the area evaluation value calculation circuitry 120 calculates, as evaluation values, the average values, variances, and kurtoses of CT values at the time of inspiration and at the time of expiration in each area.

Figure 15:
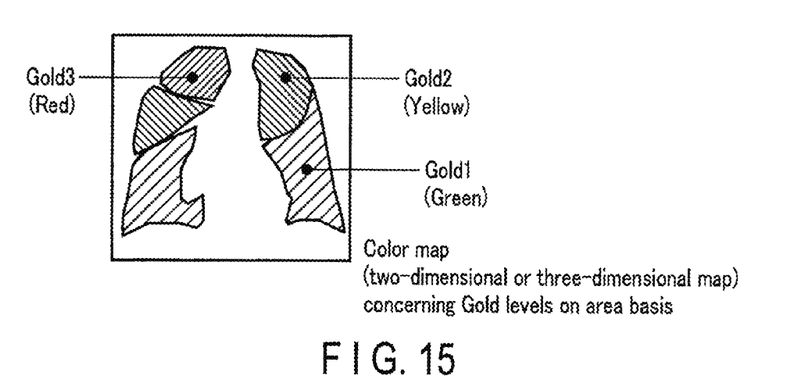
FIG. 15 is a view showing an image example concerning step R4 in FIG. 2.

In step R3, as in step V3, the severity level decision circuitry 123 decides severity levels on an area basis. A color image is generated in accordance with the severity levels and displayed, as exemplarily shown in FIG. 15. In step R3, a severity level is decided for each area based on the absolute value of the motion vector of each area and two direction components among a plurality of motion parameters including three direction components (distances) concerning the three orthogonal axes, i.e., the X-, Y-, and Z-axes, concerning the motion vector of each area.

In step R4, a severity level is decided from two or more parameters including one or more direction components of the plurality of motion parameters in step R3 and parameters selected from the average value of CT values at the time of inspiration for each area, a CT value difference, and an LAV % value. A color image may be generated and displayed in accordance with the severity levels decided in a multidimensional space in this manner.

In steps R3 and R4, a two-dimensional color image and a three-dimensional color image are generated on an area basis by using a severity table corresponding to segmented areas such as lung lobes and segments, which differs from the above severity table on a voxel or block basis.

Using a plurality of parameters such as a motion, CT value, and structure can implement more accurate diagnostic evaluation of local chronic obstructive pulmonary disease.

According to the above description, space distributions corresponding to severity levels decided on a voxel basis, a block area basis, and a segmented area basis are generated as color images. However, a severity level may be decided concerning the overall lungs. It is possible to decide a severity level concerning the overall lungs by the same processing as the method of deciding severity levels on an area basis. When deciding a severity level concerning the overall lungs, in particular, it is possible to simply presenting a GOLD value or displaying the analysis value of the overall lungs by the above technique as a point on a two-dimensional or three-dimensional severity table as well as performing color display.

Figure 18:
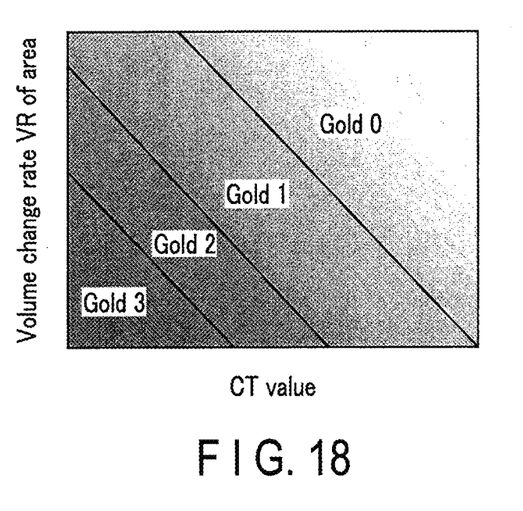
FIG. 18 is a view showing an example of severity level specifying processing using the volume change rate in FIG. 16.
Figure 19:
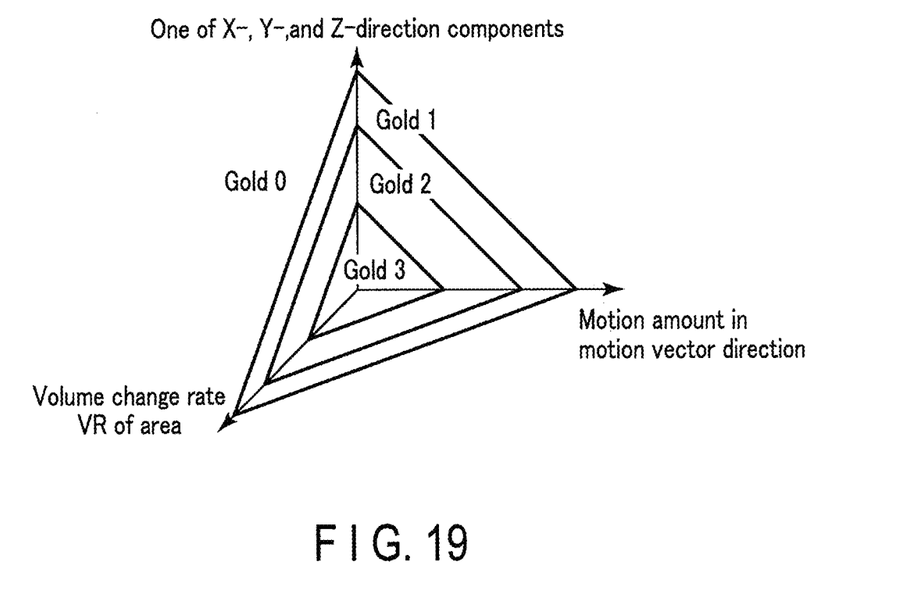
FIG. 19 is a view showing another example of a severity level using the volume change rate in FIG. 16.

As shown in FIG. 18, a severity level may be decided for each area from the volume change rate of each area and the feature value obtained from a CT value. As shown in FIG. 19, a severity level may be decided for each area from the volume change rate of each area, the distance (motion amount) of a motion vector of each area, and one of X-, Y-, and Z-direction components concerning the motion vector of each area.

Figure 20:
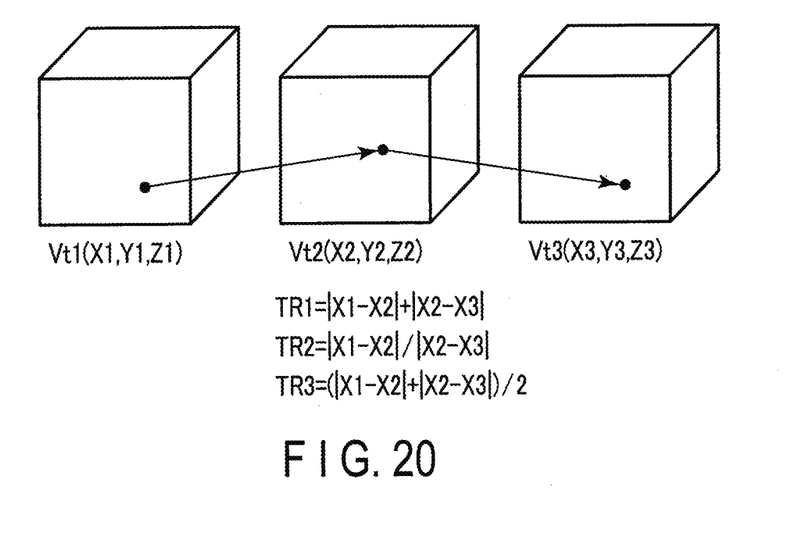
FIG. 20 is a view showing a three-phase motion amount as one of the parameters used to decide a severity level in this embodiment.

According to the above description, severity levels are decided by obtaining motion amounts and the like between two images in different respiratory phases. However, as shown in FIG. 20, severity levels may be decided by obtaining motion amounts and the like between three images in different respiratory phases Vt1, Vt2, and Vt3 or more images. As a motion amount of one of the X-, Y-, and Z-direction components concerning the motion vector of each area from three images in different respiratory phases, one of TR1, TR2, and TR3 is selected. For example, the motion amount of an X-direction component concerning a motion vector is given by $$TR1 = |X1-X2| + |X2-X3|$$

$$TR2 = |X1-X2|/|X2-X3|$$

$$TR3 = (|X1-X2| + |X2-X3|)/2$$

where X1 is the X-coordinate of a given voxel on the image in the respiratory phase Vt1, X2 is the X-coordinate of the corresponding voxel on the image in the respiratory phase Vt2, and X3 is the X-coordinate of the corresponding voxel on the image in the respiratory phase Vt3. That is, a motion amount as a parameter for deciding a severity level is obtained based on the total sum of moving distances between a plurality of images, the ratio of moving distances between the plurality of images, and the average of the moving distances between the plurality of images.

The above described "processing circuitry" means, for example, a central processing unit (CPU), a graphics processing unit (GPU), an application specific integrated circuit (ASIC), a programmable logical device (e.g., a simple programmable logic device (SPLD), a complex programmable logic device (CPLD), and a field programmable gate array (FPGA)), or the like.

Note that programs may be directly incorporated in processing circuitry instead that programs are stored in storage memory 112. In this case, the processing circuitry reads programs incorporated in circuitry and executes the programs to realizes predetermined functions.

Each function (each component) in the present embodiment is not necessary to be corresponded to a single processing circuit and may be realized by a plurality of processing circuits. To the contrary, for example, at least two functions (at least two components) may be realized by a single processing circuit. Further, a plurality of functions (a plurality of components) may be realized by a single processing circuit.

Some embodiments of the present invention have been described above. However, these embodiments are presented merely as examples and are not intended to restrict the scope of the invention. These embodiments can be carried out in various other forms, and various omissions, replacements, and alterations can be made without departing from the spirit of the invention. The embodiments and their modifications are also incorporated in the scope and the spirit of the invention as well as in the invention described in the claims and their equivalents.

The invention claimed is:

1. A medical image processing apparatus comprising:
an image storage memory configured to store data of a plurality of images in different respiratory phases which represent a morphology of an object chest portion;
a calculation circuitry configured to calculate a motion amount of a region between the plurality of images for each pixel or area;
a level decision circuitry configured to decide a level concerning a severity of chronic obstructive pulmonary disease for each pixel or area based on a combination of at least two of the motion amount, a feature value obtained from pixel values of the image, and a change rate of a size of the area; and
an output interface circuitry configured to output information concerning the decided level.

2. The medical image processing apparatus according to claim 1, wherein the feature value comprises the pixel value, a difference between the pixel values, a ratio of the number of pixels having pixel values less than a threshold to the number of pixels in the area, a variance of a pixel value distribution in the area, or an average value of pixel values in the area.

3. The medical image processing apparatus according to claim 1, further comprising a generation circuitry configured to generate a two-dimensional or three-dimensional map concerning the decided level.

4. The medical image processing apparatus according to claim 1, wherein the image comprises a two-dimensional image or a three-dimensional image.

5. The medical image processing apparatus according to claim of 1, wherein the calculation circuitry calculates a vector for the each pixel or area.

6. The medical image processing apparatus according to claim 5, wherein the motion amount is represented by one direction component or two direction components of the vector.

7. The medical image processing apparatus according to claim 5, wherein the change rate of the size of the area is calculated from a ratio of an area or volume of an area defined by a plurality of pixels of another image, the plurality of pixels respectively corresponding to a plurality of adjacent pixels of one of the plurality of images via the vector, to an area or volume of an area defined by the plurality of adjacent pixels.

8. The medical image processing apparatus according to claim 1, wherein the plurality of images include an inspiration image generated at the time of inspiration and an expiration image generated at the time of expiration, and
the motion amount, the feature value, and the change rate are calculated by using the inspiration image and the expiration image.

9. The medical image processing apparatus according to claim 1, wherein a right lung area and a left lung area of lung fields are used as the areas.

10. The medical image processing apparatus according to claim 9, wherein the right lung area and the left lung area are segmented into a plurality of lung lobe areas.

11. The medical image processing apparatus according to claim 10, wherein each of the lung lobe areas is segmented into a plurality of lung segment areas.

12. The medical image processing apparatus according to claim 1, wherein a block area as an aggregate of a predetermined number of adjacent voxels is used as the area.

13. The medical image processing apparatus according to claim 1, further comprising a registration processing circuitry configured to register anatomical positions between the plurality of images,
wherein the calculation circuitry calculates a motion amount of a region between the registered images.

14. A medical image processing apparatus comprising:
a storage memory configured to store data of first volume data and second volume data in different respiratory phases which represent a morphology of an object chest portion;
a calculation circuitry configured to calculate a motion vector of a region between the first volume data and the second volume data for each pixel or area;
a level decision circuitry configured to decide a level concerning a severity of chronic obstructive pulmonary disease for each pixel or area based on a combination of at least two of the motion vector, a feature value obtained from pixel values of the first volume data and the second volume data, and a change rate of a size of the area; and
a generation circuitry configured to generate a map indicating a spatial distribution concerning the decided levels.

15. The medical image processing apparatus according to claim 14, wherein the first volume data is acquired at the time of inspiration, and the second volume data is acquired at the time of expiration.

16. The medical image processing apparatus according to claim of 14, wherein the level decision circuitry decides the level based on the feature value and one direction component concerning the motion vector.

17. The medical image processing apparatus according to claim 14, wherein the level decision circuitry decides the level based on the feature value and two direction components concerning the motion vector.

18. The medical image processing apparatus according to claim 14, wherein the feature value comprises the pixel value, a difference between the pixel values, a ratio of the number of pixels having pixel values less than a threshold to the number of pixels in the area, a variance of a pixel value distribution in the area, or an average value of pixel values in the area.

19. The medical image processing apparatus according to claim 14, wherein as the motion vector, a vector indicating an average distance, a vector indicating an intermediate value of distances, or a vector indicating a median value of distances is selected from a plurality of vectors included in each of the areas.

20. The medical image processing apparatus according to claim 14, wherein the first volume data and the second volume data are generated by an X-ray computed tomography apparatus or a magnetic resonance imaging apparatus.

21. The medical image processing apparatus according to claim 14, wherein as the area, a lung field area is segmented into a right lung area and left lung area, the right lung area and the left lung area each are segmented into a plurality of lung lobe areas, and each of the lung lobe areas is segmented into a plurality of lung segment areas.

22. The medical image processing apparatus according to claim 14, wherein the motion vector is differentiated into a Z-axis direction component indicating a diaphragm moving direction, a Y-axis direction component indicating a sternum moving direction, and an X-axis direction component perpendicular to the Z-axis and the Y-axis.

23. The medical image processing apparatus according to claim 14, further comprising a registration processing circuitry configured to register anatomical positions between the plurality of images,
wherein the calculation circuitry calculates a motion vector of a region between the registered images.

24. The medical image processing apparatus according to claim 14, wherein the change rate of the size of the area is calculated from a ratio of an area or volume of an area defined by a plurality of voxels on the second volume data, the plurality of voxels respectively corresponding to a plurality of adjacent voxels on the first volume data via the motion vector, to an area or volume of an area defined by the plurality of adjacent voxels.

25. A medical image processing method comprising:
anatomically registering first volume data and second volume data in different respiratory phases which represent a morphology of an object chest portion;
calculating a motion vector between the registered first volume data and second volume data for each voxel or area;
deciding a level concerning a severity of chronic obstructive pulmonary disease for each pixel or area based on a combination of at least two of the motion vector, a feature value obtained from pixel values of the first volume data and the second volume data, and a change rate of a size of the area; and
generating a map indicating a spatial distribution concerning the decided levels.

* * * * *